United States Patent [19]

Deller et al.

[11] Patent Number: 5,166,120

[45] Date of Patent: Nov. 24, 1992

[54] CYLINDRICALLY FORMED CATALYST FOR THE OXYCHLORINATION OF ETHYLENE

[75] Inventors: Klaus Deller, Hainburg; Helmfried Krause, Rodenbach; Ludwig Schmidhammer, Haiming; Willibald Dafinger, Emmerting, all of Fed. Rep. of Germany

[73] Assignees: Degussa Aktiengesellschaft, Munich; Wacker-Chemie GmbH, Frankfurt am Main, both of Fed. Rep. of Germany; a part interest

[21] Appl. No.: 710,205

[22] Filed: Jun. 6, 1991

[30] Foreign Application Priority Data

Jun. 9, 1990 [DE] Fed. Rep. of Germany ....... 4018512

[51] Int. Cl.$^5$ .................... B01J 23/04; B01J 23/72; B01J 27/122
[52] U.S. Cl. ..................... 502/225; 502/345
[58] Field of Search ............... 502/225, 345

[56] References Cited

U.S. PATENT DOCUMENTS

| | | | |
|---|---|---|---|
| 4,123,467 | 10/1978 | Ramsey et al. | 260/659 A |
| 4,206,180 | 6/1980 | Ramsey et al. | 422/190 |
| 4,366,093 | 12/1982 | Shiozaki et al. | 252/477 R |
| 4,382,021 | 5/1983 | Laurer et al. | 502/225 |
| 4,511,671 | 4/1985 | Noboru et al. | 502/242 |
| 4,717,781 | 1/1988 | Imai et al. | 585/441 |
| 4,753,914 | 6/1988 | Eichhorn et al. | 502/225 |

FOREIGN PATENT DOCUMENTS

| | | |
|---|---|---|
| 0102641 | 3/1984 | European Pat. Off. |
| 2630938 | 2/1977 | Fed. Rep. of Germany |
| 3113179 | 1/1982 | Fed. Rep. of Germany |
| 3607449 | 9/1987 | Fed. Rep. of Germany |

*Primary Examiner*—W. J. Shine
*Attorney, Agent, or Firm*—Beveridge, DeGrandi & Weilacher

[57] ABSTRACT

A carrier catalyst containing copper and alkali ions on an annular carrier of surface-active material is defined by the dimensions of the carrier body and the porosity of the finished catalyst. Its total pore volume is 0.6–1.0 ml/g, pores smaller than 4 nm diameter are not present, pores of 8–20 nm diameter constitute at least 80% of the total pore volume and the remainder consists of macropores with a diameter greater than 20 nm (i.e., up to 200 nanometers). The catalyst is suitable for the production of 1,2-dichloroethane by means of the oxychlorination of ethylene.

8 Claims, 1 Drawing Sheet

CYLINDRICALLY FORMED CATALYST FOR THE OXYCHLORINATION OF ETHYLENE

INTRODUCTION TO THE INVENTION

The present invention relates to a formed carrier catalyst comprising copper ions and alkali ions on a cylindrically shaped, activated carrier. This carrier catalyst is used in particular in the selective oxychlorination of ethylene.

The oxychlorination of ethylene in a catalytic fixed bed is a known method used in industry. The catalysts used contain copper II chloride on a carrier in combination with promotors such as e.g. potassium chloride. It is particularly desirable, when carrying out the method, that the pressure drop caused by the catalyst is low, that the effective surface of the catalyst is large, and that the heat conductivity between the catalytic particles and an inert diluting agent (which is optionally present) is good.

The pressure drop across the catalyst bed is generally very high when using formed carrier catalysts since the hollow spaces in a densely packed bed are small. In regards to the shaping of the carrier material, which normally contains activated clay, aluminum silicate, silica gel or a similar surface-active material, cylindrical form bodies (hollow cylinders) are described in DE-OS 36 07 449 (EP-A 240,714) and in DE-OS 31 13 179 (U.S. Pat. No. 4,366,093), and spheres are described in DE-OS 26 30 938. However, the lowering of the pressure drop, e.g. by means of enlarging the dimensions of diameter and length of the carrier bodies, usually results in smaller conversions since this reduces the active surface of the catalyst.

Much heat is liberated in the oxychlorination reaction. This produces excessively overheated zones (hot spots) in the catalytic bed in spite of cooling the tube bundle reactors by means of the evaporation of hot pressurized water or with the aid of a heat exchanger medium (e.g., thermooil or a salt melt). The overheated zones damage the catalyst and reduce the selectivity. It was therefore suggested in DE-OS 14 93 213 that oxychlorination be carried out in a system of several series-connected reactors, that the total amount of oxygen required for oxychlorination reaction be distributed over the corresponding number of reactors, and that the reactors be filled with catalysts of differing activity stages which increase in the direction of flow. It was further provided that the oxychlorination catalyst be made leaner by means of the addition of inert material in order to avoid overheating in the catalytic bed. A method which is both technically and also economically expensive is described in U.S. Pat. No. 3,892,816, according to which the reaction is carried out in the presence of a high excess of ethylene with pure oxygen while circulating the excess, non-reacted ethylene.

Thus, in all of these prior art systems, the reaction control takes place at the expense of the space-time yield of a given system. It is also important, on account of the strongly exothermal reaction, that good heat conductivity prevails in the catalytic bed. This is usually achieved by selecting a catalyst form in which the contact surfaces between the individual catalyst particles are as large as possible, e.g. the annular form (which is obtainable, e.g. by means of extruding or tabletting) or the more economical form of column-like carriers. The conflicting problem of achieving high selectivities at low combustion rates in a given system without losses in the space-time yield, which is also a function of, among other things, the pressure drop across the reactors and of the catalytic activity, is not solved in an economical fashion by the known methods. This is especially true since the customarily used carrier material, whose pore distribution generally exhibits a pore maximum of 3 to 10 nanometers, greatly furthers the oxidation of ethylene to form undesired carbon monoxide and carbon dioxide.

SUMMARY OF THE INVENTION

One object of the present invention is to solve the problem of making available a catalyst of the described type which exhibits superior properties over known catalysts of the former state while also preserving economic aspects in regards to pressure drop, activity and selectivity.

This and other objects are achieved with a cylindrically formed carrier catalyst containing copper ions and alkali ions on an annular carrier. The annular carrier material exhibits an outside diameter of 4 to 6 mm, an inside diameter of 1 to 2 mm, and a height which is 1.7 to 3.75 times the outside diameter. Preferably the height is 2.0 to 3.00 times the outside diameter. The carrier catalyst containing the copper ions and alkali ions has a total pore volume of 0.6 to 1.0 ml/g. The pore distribution is such that pores smaller than 4 nanometers are not present. At least 80% of the total pore volume is formed by pores with a diameter of 8 to 20 nanometers and the remainder consists of pores of 4 to 8 nanometers and of macropores greater than 20 nanometers (i.e., up to 200 nanometers).

It is especially advantageous if the carrier is comprised of gamma aluminum oxide with a specific surface of 120 to 215 $m^2/g$ (BET surface) and a pore volume of 0.6 to 1.0 ml/g.

Further subject matter of the invention is constituted by the use of the carrier catalyst for the production of 1,2 dichloroethane by means of the oxychlorination of ethylene with an oxygen source (e.g., air or air enriched with oxygen) or with pure oxygen while circulating the excess, non-reacted ethylene gas.

DETAILED DESCRIPTION OF THE INVENTION

Figure 1:
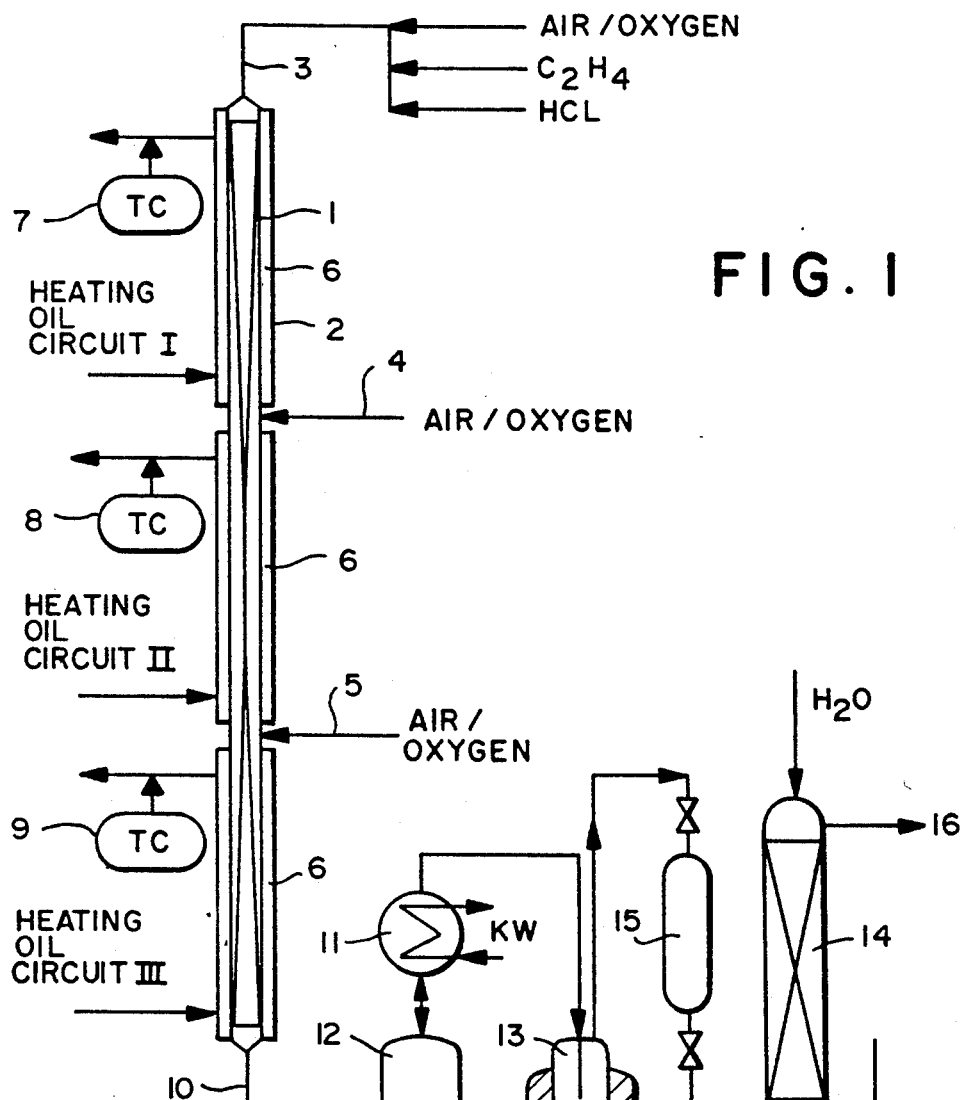
FIG. 1 is a schematic flow chart of the process of the invention.

It is generally known that the above-described pressure drop can be reduced across a bed of annular or spherical catalytic bodies by means of using larger outside diameters and/or lengths of the catalytic bodies. Such a bed is specially advantageous in regard to activity and pressure drop in comparison to beds with other geometries of catalytic bodies. Surprisingly, however, the activity or the conversion, respectively, is increased, in spite of a lowering of the active surface area, if the carrier material of the present invention is used.

The annular carrier catalyst of the present invention, containing copper ions and alkali ions and with the special shape, the described pore volume, and the described pore distribution, thus exhibits a lesser pressure drop than traditional hollow extrudates and is more active in spite of the reduced active surface area.

Lower pressure drops also increase the space-time yields because the throughput of existing plants can be more heavily loaded as a consequence. In addition, higher selectivities are obtained with carrier catalysts of the present invention and in particular the oxidation of ethylene to carbon monoxide and/or carbon dioxide is reduced thereby, which improves the yield of ethylene. This is all the more surprising because the heat conductivity between the catalytic properties should actually be poorer due to the special shape of the invention and the dimension of the carrier material according to the invention. Moreover, a person skilled in the art would not readily recognize or predict that an increase in activity takes place, in spite of a reduction of the active surface, upon switching to carrier materials with relatively large total pore volume and with the predominant part of the pores in the mesopore range. Normally the activity of a catalyst is a function of the pore distribution and the activity increases as the pore diameter decreases within certain limits.

As a result of the large pore volume, the carrier catalysts of the prevent invention also have a very long service life and deliver an extremely high specific product output with high space-time yields. The specific surface is determined according to BET in according with DIN 66131. The total pore volume is calculated from the sum of the micro-, meso- and macropore volumes. The micro- and mesopore volumes are measured by recording nitrogen isotherms and evaluating them according to BET and de Boer, Barret, Joyner and Halenda. The macropore volumes are determined by means of the mercury immersion method. These methods are known in the art.

The shaping of the carrier material can take place in a customary manner using known methods such as tabletting machines or preferably hollow extruding apparatus in which known auxiliary extruding agents (such as starch, methyl cellulose, polyethylene glycol and the like) are generally used as additives. These agents act in such a manner as to improve porosity and/or act as lubricant and/or as peptizing agent, and are deformed with the carrier material, preferably not until after a kneading process. After the shaping and the required heat treatment, which can take place in one or also in several calcining steps, the carrier is impregnated with the active components and promotors. The impregnation of the carrier with the catalytically active components takes place in accordance with customary techniques, e.g. by means of soaking with aqueous solutions in which copper II chloride and alkali chloride, usually potassium chloride, are present in the desired amounts.

The drying of the carrier catalyst is performed in air or in an atmosphere of inert gas at temperatures of 80° to 180° C.

In addition, however, the shaping step can also start with a powdery carrier catalyst which already contains the active component. Gamma aluminum oxide with a specific surface of 120–215 m$^2$/g (BET surface) and a pore volume of 0.6–1.0 ml/g is preferably used as carrier material. This enables one to obtain the stated range of specific surface area and pore volume and ultimately a finished catalyst having an aluminum oxide carrier after impregnation of the carrier with the active components.

The oxychlorination method can be carried out while using the catalyst of the present invention in a single stage or in several stages. In the preferred multistage reaction, the individual reactor feeds such as air and oxygen or hydrogen chloride are split up and supplied separately to the individual stages (see FIG. 1).

The reaction mixture exiting from the reaction zone can be returned to the reaction zone mixed with fresh hydrogen chloride, ethylene and air or oxygen, both in the one-stage and in the multistage methods of operation. The reaction products 1,2-dichloroethane and water can be separated, if necessary, totally or in part from the reaction mixture before the recycling.

Air or air enriched with oxygen or also pure oxygen can serve as oxygen sources. Water vapor is added to the oxygen-rich air in an advantageous embodiment.

A large excess of ethylene is required when using pure oxygen and the excess, non-reacted ethylene must be recirculated. This does not weaken the advantages of the carrier catalyst of the invention in any way. The temperatures in the catalyst bed normally fluctuate at values between 200° and 320° C. and the pressures at 3 to 10 absolute bars. In order to avoid temperature peaks which are too high in the catalytic bed, it is advantageous when carrying out the oxychlorination method using the carrier catalyst of the present invention to graduate the activity of the catalyst in such a manner that the activity in the reactor increases in the direction of product flow in the case of a one-stage method of operation and at least in the first and in the second stages in the case of a multistage operation. The graduation of catalytic activity can take place by means of known measures, e.g. by means of the addition of inert material as diluting agent. However, it is preferable to adjust the particular desired catalytic activity by appropriately varying the copper II chloride concentration of the catalyst and/or by varying the molar ratio of copper II chloride to alkali chloride in the catalyst.

The invention is explained further in the following examples (taken together with FIGS. 1 and 2):

EXAMPLES

Example 1

The laboratory reactor used comprises according to FIG. 1, of a vertically standing nickel tube 1 (25 mm inside width and 2000 mm length) which is surrounded by a double jacket 2 of steel. The reactor has three supply lines. Supply position 3 is located at the upper end of the reaction tube whereas supply positions 4 and 5 are laterally attached after the first and the second third of the reaction tube. Thermostatically controlled heating oil of differing temperatures are recirculated in three heating-oil circuits I to III in the hollow space 6 between nickel tube 1 and steel tube which is vertically divided into three equally long segments. The three heating and cooling circuits I to III can be temperature-controlled separately via control elements 7, 8, and 9. The control temperature is e.g. 215° C. in upper heating circuit I, e.g. 225° C. in middle heating circuit II, and e.g. 230° C. in lower heating circuit III. Reaction tube 1 is loaded in accordance with the following loading pattern with carrier catalysts (viewed from the top downward):

13 cm Berl saddles with 4 mm diameter 35 cm gamma-$Al_2O_3$ carrier with 7% $CuCl_2$ and 3% KCl 23 cm gamma-$Al_2O_3$ carrier with 20% $CuCl_2$ and 1.8% KCl 35 cm gamma-$Al_2O_3$ carrier with 10% $CuCl_2$ and 3% KCl 23 cm gamma-$Al_2O_3$ carrier with 20% $CuCl_2$ and 1.8% KCl 58 cm gamma-$Al_2O_3$ carrier with 20% $CuCl_2$ and 1.8% KCl 13 cm Berl saddles with 4 mm diameter.

The individual gas flows are supplied via calibrated rotameters. 100 Nl/h (Nl=normal liter, standard conditions for gas, standard temperature and pressure) hydrogen chloride and 58 Nl/h ethylene are first mixed and then supplied together with 57 Nl/h air via supply position 3 at the top of the reactor. A further 57 Nl/h air and 30 Nl/h air are supplied via supply lines 4 and 5 respectively. The reaction mixture leaving the reactor via line 10 is cooled in an intensive condenser 11 with water (KW=coating water; the arrows show the direction of water flow), during which partial condensation occurs. The liquid phase, consisting of 1,2-dichloroethane and reaction water, in which non-reacted hydrogen chloride is dissolved for the most part, is separated in separator 12. The non-condensable gas flow is cooled down in cold trap 13 to −25° C., during which time further condensation occurs, and is then washed free of hydrogen chloride in water scrubber 14 while HCl free gas exits through line 16. The aqueous phase from 14 is collected in 17. The two condensates from separator 12 and cold trap 13 are combined and analyzed with gas chromatography after separation of the aqueous phase by decanting. The waste gas after cold trap 13 is examined for carbon monoxide and carbon dioxide after sampling by means of a gas mouse 15 by gas chromatography. The hydrogen chloride conversion is calculated from the hydrogen chloride content in the combined aqueous phase and in the effluent of water scrubber 14. The reaction is carried out at atmospheric pressure.

Gamma-$Al_2O_3$ hollow extrudates with the following characteristics are used to produce the carrier catalysts of the present invention:

| | |
|---|---|
| Spec. total surface (BET): | 198 m$^2$/g |
| Total pore volume: | 0.86 ml/g |
| Pore distribution: | No pores < 4 nm diameter, 83% of pores with a diameter of 8-20 nm, remainder macropores > 20 nm; |
| Outside diameter: | 4.5 mm |
| Inside diameter: | 1.5 mm |
| Length: | 11 ± 2 mm. |

The catalysts are produced as follows:

(a) 7% by weight $CuCl_2$, 3% by weight KCl on gamma-$Al_2O_3$ hollow extrudates as carrier body: 270 g carrier bodies are impregnated with an aqueous solution containing 27 g $CuCl_2 \times 2H_2O$ and 9 g KCl. The drying takes place at 130° C. The finished catalyst has a BET surface of 169 m$^2$/g and a total pore volume of 0.78 ml/g.

(b) 10% by weight $CuCl_2$, 3% by weight KCl on gamma-$Al_2O_3$ hollow extrudates as carrier body: 261 g carrier bodies are impregnated with an aqueous solution containing 38.5 g $CuCl_2 \times 2H_2O$ and 9 g KCl. The drying takes place at 130° C. The finished catalyst has a BET surface of 154 m$^2$/g (c) 20% by weight $CuCl_2$, 1.8% by weight KCl on gamma-$Al_2O_3$ hollow extrudates as carrier body: 469 g carrier bodies are impregnated with an aqueous solution containing 154 g $CuCl_2 \times 2H_2O$ and 11 g KCl. The drying takes place at 130° C. The finished catalyst has a BET surface of 126 m$^2$/g and a total pore volume of 0.65 ml/g.

The amount of copper II chloride may range from 7 to 20% by weight. The amount of potassium chloride may range from 1.8 to 3% by weight.

The test results are presented in table 1.

Comparison example 1

Gamma-$Al_2O_3$ hollow extrudates with the following data are used to produce the carrier catalysts:

| | |
|---|---|
| Spec. total surface (BET): | 242 m$^2$/g |
| Total pore volume: | 0.50 ml/g |
| Pore distribution: | No pores < 2 nm diameter, 75% of pores with a diameter of 3-8 nm, remainder > 8 nm; |
| Outside diameter: | 4.5 mm |
| Inside diameter: | 1.5 mm |
| Length: | 5 ± 1 mm. |

The catalysts are produced in a manner analogous to that in example 1.

| Catalyst | BET surface | pore volume |
|---|---|---|
| 7% by wt. $CuCl_2$, 3% by wt. KCl | 197 m$^2$/g | 0.43 ml/g |
| 10% by wt. $CuCl_2$, 3% by wt. KCl | 168 m$^2$/g | 0.38 ml/g |
| 20% by wt. $CuCl_2$, 1.8% by wt. KCl | 110 m$^2$/g | 0.29 ml/g |

The results are presented in table 1.

Comparison example 1b

Gamma-$Al_2O_3$ spheres (4-6 mm diameter) with the following characteristics are used to produce the carrier catalysts:

| | |
|---|---|
| Spec. total surface (BET): | 222 m$^2$/g |
| Total pore volume: | 0.60 ml/g |
| Pore distribution: | No pores < 2 nm diameter, 60% of pores with a diameter of 2-8 nm, remainder > 8 nm; |

The catalysts are produced in a manner analogous to that in example 1.

| Catalyst | BET surface | pore volume |
|---|---|---|
| 7% by wt. $CuCl_2$, 3% by wt. KCl | 195 m$^2$/g | 0.54 ml/g |
| 10% by wt. $CuCl_2$, 3% by wt. KCl | 179 m$^2$/g | 0.49 ml/g |
| 20% by wt. $CuCl_2$, 1.8% by wt. KCl | 130 m$^2$/g | 0.41 ml/g |

The results are presented in table 1.

TABLE 1

| | Example 1 | Reference example 1a | Reference example 1b |
|---|---|---|---|
| Organic condensate | 162.4 cm$^3$/h | 153.2 cm$^3$/h | 149.0 cm$^3$/h |
| Aqueous condensate | 47.6 cm$^3$/h | 38.5 cm$^3$/h | 36.8 cm$^3$/h |
| Amount of waste gas | 135.4 Nl/h | 139.5 Nl/h | 145.9 Nl/h |
| HCl conversion | 91.9% | 88.7% | 85.2% |
| Waste gas analysis | | | |
| CO content | 0.80 Vol % | 0.98 Vol % | 1.71 Vol % |
| $CO_2$ content | 0.62 Vol % | 1.25 Vol % | 1.55 Vol % |
| Analysis of the orq. | | | |

TABLE 1-continued

|  | Example 1 | Reference example 1a | Reference example 1b |
|---|---|---|---|
| condensate |  |  |  |
| Ethyl chloride* | 510 | 1600 | 1050 |
| Trans-1,2-dichloroethylene* | 180 | 300 | 500 |
| 1,1-dichloroethane* | 150 | 130 | 180 |
| Carbon tetrachloride* | 2290 | 2300 | 3500 |
| Cis-1,2-dichloroethylene* | 560 | 980 | 1490 |
| Chloroform* | 1090 | 1890 | 2540 |
| 1,2-dichloroethane** | 97.88 | 96.40 | 95.41 |
| Chloral* | 1540 | 2100 | 2200 |
| 1,1,2-trichloroethane** | 1.485 | 2.65 | 3.15 |

Key:
Vol % = % by volume
* = ppm by weight
** = % by weight

The data in table 1 show the great technical progress in regards to activity, product selectivity, and combustion rate when using the carrier catalyst of the present invention in comparison to traditional catalysts, in which the spherical catalysts are inferior (as was to be expected) to annular catalysts for known reasons.

Example 2

A reactor system was used which consisted of three equally large, series-connected tube bundle reactors. Each reactor contained 3,200 nickel tubes with an inside width of 27.5 mm. The catalyst of example 1 was in the nickel tubes, which exhibited an activity profile which increased in the direction of flow. Gamma-$Al_2O_3$ was used as carrier material, which was present in the form of rings with the following dimensions:

Outside diameter: 4.5 mm
Inside diameter: 1.5 mm
Length: 11±2 mm

An activity profile extending over the length of the reactor divided into thirds increasing in the direction of flow was realized in that in the beginning one third section of each reactor, the concentration of copper II chloride was 7% by weight and the concentration of potassium chloride area was 3% by weight; in each middle third section 10% by weight $CuCl_2$ and 3% by weight KCl; and in each last third section approximately 20% by weight $CuCl_2$ and 1.8% by weight KCl were present. The catalyst volume was 6.8 m² per reactor. The total pore volume of the carrier catalyst was at values of 0.78, 0.72 and 0.65 ml/g, depending on the charge of active component. Approximately 83% of the pore volume was formed by pores with a diameter of 8 to 20 nanometers.

The specific surface of the carrier catalyst was at values of 169, 154 and 126 m²/g, depending on the charge with the active components. The nickel tubes were surrounded with an outer jacket in which water was present as a cooling medium for removing the reaction heat being liberated. This water was under a pressure of 19 absolute bars in the first reactor, 21 absolute bars in the second reactor and 24 absolute bars in the third reactor.

Air, used as the oxygen source, was brought to an oxygen content of 30% by volume by means of the addition of pure oxygen. A mixture of 437.5 kmoles/h hydrogen chloride, 220 kmoles/h ethylene and 160 kmoles/h air (enriched to 30% by volume oxygen) was introduced into the first reactor at controlled pressures of 8 absolute bars. The air enriched with oxygen was loaded with 48 kmoles/h water vapor after having been prewarmed to 180° C. before being mixed with the other reactants. The temperature of the reaction mixture prior to entry into the first reactor was 135° C.

The reaction mixture leaving the first reactor was loaded, before entering into the second reactor, with 172 kmoles/h air enriched to 30% by volume oxygen. Finally, another 70 kmoles/h air enriched to 30% by volume oxygen was supplied to the reaction mixture between the second and the third reactor. The system pressure before the first reactor was 6.4 absolute bars. The pressure drop across the reactors was 0.37 bar in the first reactor, 0.50 bar in the second reactor, and 0.54 bar in the third reactor. The hot-spot temperatures were about 289° C. in the first reactor, about 280° C. in the second reactor, and about 235° C. in the third reactor.

The reaction mixture leaving the third reactor, with an average temperature of 220° C., was cooled and condensed. The liquid condensate was separated, in a subsequently connected-in decanter, into an organic and an aqueous phase. The organic phase had the following composition:

| Ethyl chloride | 0.22% by weight |
|---|---|
| 1,1-dichloroethane | 0.01% by weight |
| Chloroform | 0.04% by weight |
| Carbon tetrachloride | 0.07% by weight |
| Dichloroethylene | 0.01% by weight |
| Chloral | 0.20% by weight |
| 1,1,2-trichloroethane | 0.45% by weight |
| Others | 0.10% by weight |
| 1,2-dichloroethane | 98.90% by weight. |

The analysis of the condensed aqueous phase yielded:

| Hydrogen chloride | 1.94% by weight |
|---|---|
| Chloral hydrate | 0.38% by weight |
| 1,2-dichloroethane | 0.58% by weight. |

A conversion of hydrogen chloride of 99.4% is thus calculated from the concentration of hydrogen chloride.

The analysis of the non-condensable waste-gas current (essentially nitrogen from the air) yielded the following concentration of ethylene combustion products:

| Carbon monoxide: | 1.14% by volume |
|---|---|
| Carbon dioxide: | 0.96% by volume. |

The production rate was 21,500 kg of 1,2-dichloroethane per hour. The space-time yield was thus about 1,054 kg of 1,2-dichloroethane per m² catalyst×hour, related to all 3 reactors.

An average specific product yield of 17,850 tons 1,2-dichloroethane per m² catalyst, related all 3 reactors, was achieved. The catalyst in the first reactor achieved an operation time of 8,400 hours, in the second reactor of 24,800 hours, and in the third reactor of 17,600 hours.

Comparison example 2

The method of operation of example 2 was repeated with the catalyst of comparison example 1a:

| Outside diameter of the rings: | 4.5 mm |
|---|---|

-continued

| Inside diameter of the rings: | 1.5 mm |
| Length of the rings: | 5 ± 1 mm. |

The specific surface was 197, 168 and 110 m$^2$/g, depending on the concentration of active components; the total pore volume was about 0.43, 0.38 and 0.29 ml/g; and 75% of the pores exhibited a range of 3 to 8 nanometers diameter.

The concentrations of active components as well as the filling plan were analogous to example 2. Due to a higher pressure drop via the reactors, the throughput of the system had to be cut back by a total of 15%, which took place in a uniform manner, relative to the individual charging of the 3 reactors, according to example 2.

With the same back pressure at the end of the reaction system as in example 2, the system pressure before the first reactor, despite the flow reduction, reached the same value of 6.4 absolute bars, which limited the total throughput in an upward direction. The pressure drops and the temperatures in the individual reactors were:

| In the first reactor: | 0.57 bar hot spot 298° C. |
| In the second reactor: | 0.64 bar hot spot 291° C. |
| In the third reactor: | 0.70 bar hot spot 245° C. |

The individual product flows and waste-gas flows had the following composition:

Aqueous phase: 4.8% by weight hydrogen chloride corresponding to a hydrogen chloride conversion of approximately 98.5% by weight.

| Organic phase: | |
|---|---|
| Ethylene chloride | 0.65% by weight |
| 1,1-dichoroethane | 0.01% by weight |
| Chloroform | 0.08% by weight |
| Carbon tetrachloride | 0.12% by weight |
| Dichloroethylene | 0.02% by weight |
| Chloral | 0.35% by weight |
| 1,1,2-trichloroethane | 0.65% by weight |
| Others | 0.15% by weight |
| 1,2-dichloroethane | 97.97% by weight |
| Waste gas: | |
| Carbon monoxide: | 1.83% by volume |
| Carbon dioxide: | 1.55% by volume |

The production rate was 18,275 kg of 1,2-dichloroethane per hour. The space-time yield was thus about 896 kg of 1,2-dichloroethane per m$^2$ catalyst × hour, related to all 3 reactors. An average specific product yield of 15,844 tons 1,2-dichloroethane per m$^2$ catalyst, related to all 3 reactors, was achieved and, in spite of a low total throughput, the catalyst in the first reactor achieved an operation time of only 9,100 hours, 25,600 hours in the second reactor, and 18,300 hours in the third reactor.

The results of example 2 illustrate the technical advance of the catalyst of the present invention over traditional catalysts in regards to activity, product selectivity, combustion rate (and therewith ethylene yield), pressure drop (and therewith space-time yield), and specific product output per m$^2$ catalyst.

Example 3

The laboratory reactor described in example 1 and shown in FIG. 1 was used. Likewise, the same catalyst and the same leading pattern as in example 1 were used. The reaction conditions were likewise analogous to example 1 with the exception that, instead of air as oxygen source, pure oxygen was used.

In order to approximately simulate the operating characteristics of recycle gas in the ethylene-rich range on account of a lacking recycle-gas compressor (according to U.S. Pat. No. 3,892,816), the following amounts of reactants were used:

100 Nl/h hydrogen chloride, mixed with 390 Nl/h ethylene, and
10.5 Nl/h oxygen via supply position 3,
10.5 Nl/h oxygen via supply position 4,
5.25 Nl/h oxygen via supply position 5.

The workup and analytic evaluation of the reaction product took place in a manner analogous to that in example 1.

The results are presented in table 2.

Comparison example 3

A procedure analogous to that of example 3 was used; however, the catalyst of reference example 1a was used. The results are presented in table 2.

TABLE 2

| | Example 3 | Comparative example 3 |
|---|---|---|
| Organic condensate | 169.4 cm$^3$/h | 169.0 cm |
| Aqueous condensate | 50.4 cm$^3$/h | 50.5 cm$^3$/h |
| Amount of waste gas | 357 Nl/h | 335 Nl/h |
| HCl conversion | 99.8% | 99.7% |
| Waste-gas analysis | | |
| CO content | 0.15 Vol % | 0.36 Vol % |
| CO$_2$ content | 0.30 Vol % | 0.63 Vol % |
| Analysis of the org. condensate | | |
| Ethyl chloride* | 390. | 1320 |
| Trans-1,2-dichloroethylene* | <1 | <1 |
| 1,1-dichloroethane* | 100 | 180 |
| Carbon tetrachloride* | 930 | 1490 |
| Cis-1,2-dichloroethylene* | <1 | <1 |
| Chloroform* | 690 | 1080 |
| 1,2-dichloroethane** | 99.68 | 99.39 |
| Chloral* | 640 | 960 |
| 1,1,2-trichloroethane* | 410 | 1080 |

Key:
Vol % = % by volume
* = ppm by weight
** = % by weight

The results of the oxygen operating characteristics in the so-called fuel rich range show that the catalyst of the present invention achieves a great technical advance, especially in regard to product selectivity and combustion rate, even in the case of pure oxygen operating characteristics. The product selectivity is by nature higher and the combustion rate lower if, instead of air, pure oxygen and an extremely high excess of ethylene are used, since ethylene strongly favors the removal of heat in comparison to nitrogen (from the air) on account of its much higher specific heat capacity.

As a result of the extremely high excess of ethylene required in oxygen operation relative to the stoichiometry to hydrogen chloride, the conversion of hydrogen chloride is also necessarily higher than in the case of air operation.

Figure 2:
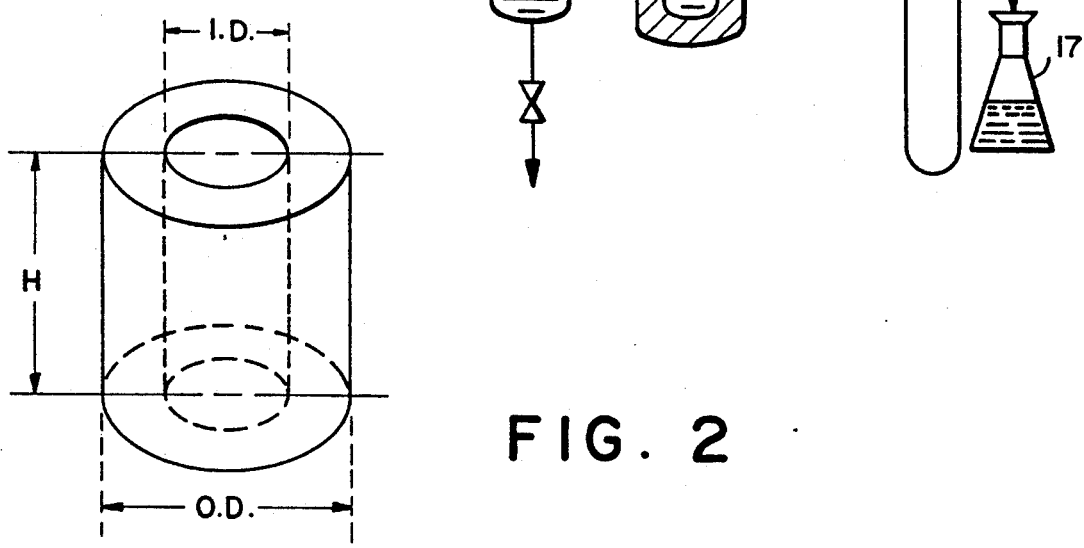
FIG. 2 is a schematic view of a representative example of the cylindrically formed catalyst on an annular carrier.

FIG. 2 shows a schematic view of a representative example of the cylindrically formed catalyst on an annular carrier. The annular carrier material exhibits an outside diameter (O.D.) of 4 to 6 mm, an inside diameter (I.D.) of 1 to 2 mm, and a height (H) which is 1.7 to 3.75 times the outside diameter. Preferably the height is 2.0 to 3.00 times the outside diameter. The carrier catalyst containing the copper ions and alkali ions has a total pore volume of 0.6 to 1.0 ml/g. The pore distribution is such that pores smaller than 4 nanometers are not present. At least 80% of the total pore volume is formed by pores with a diameter of 8 to 20 nanometers and the remainder consists of pores of 4 to 8 nanometers and of macropores greater than 20 nanometers (i.e., up to 200 nanometers).

Further variations and modifications of the invention will become apparent to those skilled in the art from the foregoing and are intended to be encompassed by the claims appended hereto.

What is claimed:

1. A cylindrically formed carrier catalyst comprising copper ions and alkali ions on an annular carrier of surface-active material, wherein said annular carrier has an outside diameter of 4 to 6 mm, an inside diameter of 1 to 2 mm, and a height which is 1.7 to 3.75 times the outside diameter, and wherein said carrier catalyst has a total pore volume of 0.6 to 1.0 ml/g and contains no pores smaller than 4 nanometers, at least 80% of said total pore volume is formed by pores with a diameter of 8 to 20 nanometers and the remainder consists of macropores having a diameter greater than 20 nanometers and up to 200 nanometers.

2. The carrier catalyst according to claim 1, wherein said annular carrier has a height which is 2.0 to 3.0 times the outside diameter.

3. The carrier catalyst according to claim 1, wherein said annular carrier further comprises gamma aluminum oxide with a BET specific surface area of 120 to 215 $m^2/g$ and a pore volume of 0.6 to 1.0 ml/g.

4. The carrier catalyst according to claim 1, wherein said copper ions are copper II chloride.

5. The carrier catalyst according to claim 4, wherein said copper II chloride is present at 7 to 20% by weight.

6. The carrier catalyst according to claim 1, wherein said alkali ions are alkali chlorides.

7. The carrier catalyst according to claim 6, wherein said alkali chloride is potassium chloride.

8. The carrier catalyst according to claim 7, wherein said potassium chloride is present at 1.8 to 3% by weight.

* * * * *